(12) United States Patent
Lorant

(10) Patent No.: US 6,344,204 B1
(45) Date of Patent: Feb. 5, 2002

(54) FLUID COSMETIC AND/OR DERMATOLOGICAL COMPOSITION IN THE FORM OF A WATER-IN-OIL EMULSION

(75) Inventor: Raluca Lorant, Thiais (FR)

(73) Assignee: L'Oreal, Paris (FR)

(*) Notice: Subject to any disclaimer, the term of this patent is extended or adjusted under 35 U.S.C. 154(b) by 0 days.

(21) Appl. No.: 09/489,842

(22) Filed: Jan. 24, 2000

(30) Foreign Application Priority Data

Feb. 8, 1999 (FR) .............................................. 99 01446

(51) Int. Cl.[7] .............................. A61K 6/00; A61K 7/00
(52) U.S. Cl. ..................... 424/401; 424/400; 424/70.1; 424/70.11; 424/70.12; 424/78.08; 424/434
(58) Field of Search ................................ 424/401, 400, 424/70.1, 70.11, 70.12, 78.08, 434

(56) References Cited

U.S. PATENT DOCUMENTS 5,849,275 A * 12/1998 Calello et al. ................ 424/64
5,882,665 A * 3/1999 Meyers et al. ............... 424/401
6,001,377 A * 12/1999 SaNogueira, Jr. et al. .. 424/401

FOREIGN PATENT DOCUMENTS

| EP | 0 516 547 | 12/1992 |
|---|---|---|
| WO | WO 96/14047 | 5/1996 |

\* cited by examiner

*Primary Examiner*—Thurman K. Page
*Assistant Examiner*—Liliana Di Nola-Baron
(74) *Attorney, Agent, or Firm*—Oblon, Spivak, McClelland, Maier & Neustadt, P.C.

(57) ABSTRACT

A cosmetic and/or dermatological composition in the form of a water-in-oil emulsion comprising (1) at least one silicone emulsifier, (2) at least one branched-chain hydrocarbonaceous oil and (3) at least one volatile silicone oil, the total amount of branched-chain hydrocarbonaceous oil and of volatile silicone oil representing at least 50% by weight of the oily phase. This composition may be used, for example, for caring for, making up, cleansing and/or removing make-up from the skin, mucous membranes, eyes and/or hair.

14 Claims, No Drawings

FLUID COSMETIC AND/OR DERMATOLOGICAL COMPOSITION IN THE FORM OF A WATER-IN-OIL EMULSION

BACKGROUND OF THE INVENTION

1. Field of the Invention

The present invention relates to a cosmetic and/or dermatological composition in the form of a fluid water-in-oil emulsion comprising a silicone emulsifier, at least one branched-chain hydrocarbonaceous oil and at least one volatile silicone oil and to its uses in caring for, making up, cleansing and/or removing make-up from the skin, mucous membranes, eyes and/or hair and in treating dry skin.

2. Description of the Background

In the cosmetics field, it is commonplace to use creams composed of a water-in-oil (W/O) emulsion comprising an aqueous phase dispersed in an oily phase. These emulsions comprise a continuous oily phase and therefore make it possible to form, at the surface of the skin, a lipid film which prevents transepidermal water loss and protects the skin from external attacks. These emulsions are particularly suitable for protecting and nourishing the skin and in particular for treating dry skin.

However, these emulsions, because of their "heavy" texture, lack freshness and fluidity and are difficult to work. They leave a greasy and sticky film on the skin. In addition, if the amount of internal (aqueous) phase is increased, so as to contribute more freshness and a less greasy feel, this results in the production of creams which are often compact and difficult to spread.

The need consequently remains for a composition in the form of a W/O emulsion which is sufficiently fluid to have a fresh feel, which is pleasant on application and which is easy to spread while retaining the emollient properties of emulsions with an external oily phase.

SUMMARY OF THE INVENTION

The inventors have now discovered, surprisingly, that a composition in the form of a water-in-oil emulsion comprising the combination of a branched-chain hydrocarbonaceous oil and of a volatile silicone oil in an amount representing at least 50% of the oily phase makes it possible to obtain a fluid composition which is light on application while retaining the usual properties of W/O emulsions.

Thus, the present invention provides a cosmetic and/or dermatological composition, comprising:
  an aqueous phase dispersed in an oily phase,
  at least one silicone emulsifier,
  at least one branched-chain hydrocarbonaceous oil,
  at least one volatile silicone oil, and
  at least one polyol alkyl ester,
    where the total amount of the branched-chain hydrocarbonaceous oil and of volatile silicone oil comprises at least 50% by weight of the oily phase The present invention also provides a method of caring for, making up, removing make-up from and/or cleansing the skin, mucous membranes and/or hair, comprising applying the inventive composition to skin, mucous membranes and/or hair The present invention also provides a method of preparing the inventive composition A more complete appreciation of the invention and many of the attendant advantages thereof will be readily obtained as the same becomes better understood by reference to the following detailed description.

DETAILED DESCRIPTION OF THE INVENTION

The composition according to the present invention is fluid and exhibits the advantage of being light and fresh on application while leaving the skin soft, matt and non-sticky.

Mention may be made, as silicone emulsifiers which can enter into the composition according to the invention, of dimethicone copolyols and alkyl dimethicone copolyols. Mention may be made, as dimethicone copolyol, of, for example, the mixture of dimethicone copolyol, of cyclomethicone and of water (10/88/2) sold by Dow Corning under the name DC3225C or DC2-5225C. According to a preferred embodiment of the invention, use is made, as silicone emulsifier, of an alkyl dimethicone copolyol having an alkyl radical comprising from 10 to 22 carbon atoms, such as cetyl dimethicone copolyol, for example the product sold under the name Abil EM-90 by Goldschmidt and the mixture of dimethicone copolyol and of cyclopentasiloxane (85/15) sold under the name Abil EM-97 by Goldschmidt; lauryl dimethicone copolyol, for example the mixture of approximately 91% lauryl dimethicone copolyol and of approximately 9% isostearyl alcohol sold under the name Q2-5200 by Dow Corning; and their mixtures.

The silicone emulsifier is preferably used in a proportion as active material (that is to say, for example, as dimethicone copolyol or alkyl dimethicone copolyol) ranging from 0.5 to 10% and preferably from 1 to 6% by weight with respect to the total weight of the composition. These ranges include all specific values and subranges therebetween, such as 2, 3, 5 and 8% by weight.

The oily phase of the composition according to the invention comprises at least one branched-chain hydrocarbonaceous oil and at least one volatile silicone oil.

The branched-chain hydrocarbonaceous oil comprises from 10 to 20 carbon atoms and can be chosen, for example, from the group consisting of isohexadecane, isododecane, isoparaffins and their mixtures.

The volatile silicone oil can be chosen, for example, from cyclic or linear polydimethylsiloxanes and their mixtures. The cyclic polydimethylsiloxanes or cyclomethicones comprise from approximately 3 to 9 carbon atoms and preferably from 4 to 6 carbon atoms and can be, for example, cyclohexadimethylsiloxane and cyclopentadimethylsiloxane. The volatile linear polydimethylsiloxanes preferably comprise from approximately 3 to 9 carbon atoms. The volatile linear polydimethylsiloxanes generally have a viscosity at 25° C. of less than or equal to 5 cSt, whereas the cyclomethicones generally have a viscosity at 25° C. of less than or equal to 10 cSt.

The total amount of branched-chain hydrocarbonaceous oil(s) and of volatile silicone oil(s) represents at least 50% by weight of the oily phase, it being possible for the ratio of the amount of one type of oil to that of the other type of oil to vary to a large extent from the time that each oil is present, the concentration of each type of oil preferably being at least 1% by weight with respect to the total weight of the composition. Preferably, the total amount of branched-chain hydrocarbonaceous oil(s) and of volatile silicone oil(s) ranges from 60 to 100% by weight with respect to the total weight of the oily phase.

The oily phase can additionally comprise any fatty substance and in particular oils conventionally used in the cosmetics or dermatological fields. The other oils capable of being present in the oily phase can be, for example, oils of vegetable origin, such as apricot kernel oil and perhydrosqualene, synthetic oils, such as fatty esters, non-volatile silicone oils and fluorinated oils. The other fatty substances capable of being present in the oily phase can be, for example, fatty acids and fatty alcohols.

The oily phase of the emulsion can represent, for example, from 8 to 60% by weight and better still from 15 to 50% by weight with respect to the total weight of the composition. These ranges includes all specific value and subranges therebetween, such as 10, 12, 20, 30, 40 and 50% by weight.

According to a specific embodiment of the invention, the composition can additionally comprise one or more polyol alkyl esters. Mention may in particular be made, as polyol alkyl ester which can be used in the composition of the invention, of glycerol and/or sorbitan esters, for example polyglycerol isostearate, such as the product sold under the name Isolan GI 34 by Goldschmidt, sorbitan isostearate, such as the product sold under the name Arlacel 987 by ICI, glycerol sorbitan isostearate, such as the product sold under the name Arlacel 986 by ICI, the mixture of sorbitan isostearate and of polyglycerol isostearate, such as the product sold under the name Arlacel 1690 by ICI, and their mixtures.

When the composition comprises one or more polyol alkyl esters, the amount of polyol alkyl ester(s) can range, for example, from 0.05 to 5% and preferably from 0.1 to 1% by weight with respect to the total weight of the composition. These ranges includes all specific values and subranges therebetween, such as 0.2, 0.5, 2, 3 and 4% by weight.

The composition of the invention can optionally also comprise one or more fillers. The filler or fillers can be chosen, for example, from the group formed by polyamide particles, in particular those sold under the name Orgasol by Atochem; polyethylene powders, microspheres based on acrylic copolymers, such as those made of ethylene glycol dimethacrylate/lauryl methacrylate copolymer which are sold by Dow Corning under the name of Polytrap; expanded powders, such as hollow microspheres and in particular the microspheres sold under the trade name Expancel by Kemanord Plast or under the trade name Micropearl F 80 ED by Matsumoto; powders formed of natural organic materials, such as maize, wheat or rice starches, which may or may not be crosslinked, such as the powders formed of starch which is crosslinked by octenylsuccinic anhydride which are sold under the name Dry-Flo by National Starch; silicone resin microbeads, such as those sold under the name Tospearl by Toshiba Silicone; and their mixtures.

The filler is preferably chosen from the microspheres sold under the trade name Expancel, which are particles of expanded terpolymer of vinylidene chloride, of acrylonitrile and of methacrylate, and in particular those sold under the references 551 DE 50 (particle size of approximately 40 $\mu$m), 551 DE 20 (particle size of approximately 30 $\mu$m and density of approximately 65 kg/m$^3$), 551 DE 12 (particle size of approximately 12 $\mu$m), 551 DE 80 (particle size of approximately 80 $\mu$m) and 461 DE 50 (particle size of approximately 50 $\mu$m). Use may also be made of microspheres formed of the same expanded terpolymer having a particle size of approximately 18 $\mu$m and a density of approximately 70 kg/m$^3$, known below as EL 23. Use may also be made of a mixture of these various particles.

The terpolymer particles indicated above can be dry or hydrated and can be obtained, for example, according to the processes of Patents and Patent Applications EP-A-056,219, EP-A-348,372, EP-A-486,080, EP-A-320,473, EP-A-1 12,807 and U.S. Pat. No. 3,615,972. Each of these documents is incorporated herein by reference.

When the composition comprises fillers, the amount of filler(s) in the composition according to the invention can preferably range from 0.01% to 15% and better still from 0.1 to 5% by weight with respect to the total weight of the composition. These ranges include all specific values and subranges therebetween, such as 0.02, 0.05, 0.1, 0.5, 2, 8, 10 and 12% by weight.

The composition according to the invention can additionally comprise one or more salts and in particular a magnesium salt, such as magnesium sulphate. The amount of salt(s) can range, for example, from 0.1 to 5% and preferably from 0.5 to 1% by weight with respect to the total weight of the composition. These ranges include all specific values and subranges therebetween, such as 0.2, 1.5, 2, 3 and 4% by weight.

In addition, in a known way, the compositions of the invention can comprise adjuvants usual in the cosmetics or dermatological field, such as hydrophilic or lipophilic active principles, preservatives, antioxidants, fragrances, solvents, fillers, screening agents, colouring materials (pigments or dyes), basic agents (triethanolamine), acidic agents and lipid vesicles. These adjuvants are used in the proportions usual in the cosmetics or dermatological field, for example from 0.01 to 30% of the total weight of the composition, and they are, depending on their nature, introduced into the aqueous phase or into the oily phase of the emulsion or into vesicles. These adjuvants and their concentrations must be such that they do not modify the property desired for the composition.

According to a specific embodiment of the invention, the composition is preferably fluid, that is to say that it has a viscosity ranging from approximately 0.2 to 3 Pa·s (2 to 30 poises) and preferably from 0.6 to 2 Pa·s (6 to 20 poises), this viscosity being measured at approximately 25° C. using a "Rheomat Metler" viscometer equipped with a 2 rotor (for viscosities of less than 0.7 Pa·s, i.e., 7 poises) or with a 3 rotor (for viscosities of greater than 0.7 Pa·s).

The cosmetic or dermatological composition according to the invention advantageously comprises a physiologically acceptable medium, that is to say a medium compatible with the skin, mucous membranes, scalp, eyes and/or hair. It can be used in particular in caring for, making up (with the addition of pigments), removing make-up from and/or cleansing the skin, mucous membranes, eyes and/or hair.

The invention consequently also relates to the cosmetic use of the composition as defined above in caring for, making up, removing make-up from and/or cleansing the skin, mucous membranes and/or hair.

Because it exhibits an external oily phase, the composition according to the invention can also advantageously constitute a composition for caring for dry skin.

A further subject-matter of the invention is the use of the composition as defined above in the preparation of a composition intended for the treatment of dry skin.

The composition according to the invention also has the advantage of making it possible to treat and/or cleanse the skin without attacking it, these compositions being particularly well suited to cleansing the skin, in particular dry and sensitive skin.

The invention also relates to a cosmetic process for treating and/or cleansing the skin, which consists in applying a composition as defined above to the skin.

EXAMPLES

Having generally described this invention, a further understanding can be obtained by reference to certain specific examples which are provided herein for purposes of illustration only and are not intended to be limiting unless otherwise specified. The proportions by weight are given as percentage by weight with respect to the total weight of the composition.

Example 1

| Softening fluid | |
| --- | --- |
| Oily phase: | |
| Cetyl dimethicone copolyol | 2% |
| Isohexadecane | 15% |
| Polyglyceryl-4 isostearate | 0.5% |
| Cyclohexamethicone | 10% |
| Filler: | |
| Expancel 551 | 1% |
| Aqueous phase: | |
| Glycerol | 5% |
| Magnesium sulphate | 0.5% |
| Preservatives | 0.4% |
| Water q.s. for | 100% |

Procedure: The filler is dispersed in the oily phase using a spatula and then the aqueous phase is dispersed very slowly, with vigorous stirring, in the mixture obtained.

The viscosity of this milk, measured at approximately 25° C. using a "Rheomat Metler" viscometer equipped with a 2 rotor, is equal to approximately 7 poises (0.7 Pa·s).

The milk obtained is very soft on application, simultaneously rich and fresh, and nongreasy, and it rapidly penetrates into the skin, which it leaves soft, matt and supple.

Example 2

| Care fluid for dry skin | |
| --- | --- |
| Oily phase: | |
| Cetyl dimethicone copolyol | 1.5% |
| Polyglyceryl-4 isostearate | 0.5% |
| Isohexadecane | 5% |
| Cyclohexamethicone | 10% |
| Perhydrosqualene | 10.5% |
| Filler: | |
| Expancel 551 | 0.5% |
| Crosslinked starch (Dry Flo) | 2% |
| Aqueous phase: | |
| Glycerol | 5% |
| Magnesium sulphate | 0.5% |
| Preservatives | 0.4% |
| Water q.s. for | 100% |

Procedure: The filler is dispersed in the oily phase using a spatula and then the aqueous phase is dispersed very slowly, with vigorous stirring, in the mixture obtained.

A milk is obtained, the viscosity of which, measured at approximately 25° C. using a "Rheomat Metler" viscometer equipped with a 3 rotor, is approximately 16 poises (1.6 Pa·s).

This thick milk is creamy, soft and rich on application. It easily penetrates, immediately contributing a soothing nutritious effect.

Example 3

| Softening fluid foundation | |
| --- | --- |
| Oily phase: | |
| Cetyl dimethicone copolyol | 2% |
| Isohexadecane | 15% |
| Polyglyceryl-4 isostearate | 0.5% |
| Cyclohexamethicone | 10% |
| Filler: | |
| Brown, red and yellow pigments | 5% |
| Aqueous phase: | |
| Glycerol | 5% |
| Magnesium sulphate | 0.5% |
| Preservatives | 0.4% |
| Water q.s. for | 100% |

Procedure: The filler is dispersed in the oily phase using a spatula and then the aqueous phase is dispersed very slowly, with vigorous stirring, in the mixture obtained.

A fluid foundation is thus obtained which is very soft on application and easy to spread. It gives a homogeneous, matt and natural make-up result. Its viscosity, measured at approximately 25° C. using a "Rheomat Metler" viscometer equipped with a 3 rotor, is approximately 10 poises (1 Pa·s).

Obviously, numerous modifications and variations of the present invention are possible in light of the above teachings. It is therefore to be understood that within the scope of the appended claims, the invention may be practiced otherwise than as specifically described herein.

This application is based on French Patent Application Serial No. 99-01446, filed on Feb. 8, 1999, and incorporated herein by reference in its entirety.

What is claimed is:

1. A cosmetic and/or dermatological composition, comprising:
    an aqueous phase dispersed in an oily phase,
    at least one silicone emulsifier,
    at least one branched-chain hydrocarbonaceous oil,
    at least one volatile silicone oil, and
    at least one polyol alkyl ester,
        wherein the total amount of the branched-chain hydrocarbonaceous oil and of volatile silicone oil comprises at least 50% by weight of the oily phase.

2. The composition of claim 1, wherein the silicone emulsifier is an alkyl dimethicone copolyol comprising an alkyl radical having from 10 to 22 carbon atoms.

3. The composition of claim 1, wherein the silicone emulsifier is selected from the group consisting of cetyl dimethicone copolyol, lauryl dimethicone copolyol and mixtures thereof.

4. The composition of claim 1, wherein the silicone emulsifier comprises 0.5 to 10% by weight with respect to the total weight of the composition.

5. The composition of claim 1, wherein the branched-chain hydrocarbonaceous oil is chosen from the group consisting of isohexadecane, isododecane, isoparaffins, and mixtures thereof.

6. The composition of claim 1, wherein the total amount of branched-chain hydrocarbonaceous oil(s) and of volatile silicone oil(s) comprises from 60 to 100% by weight of the oily phase.

7. The composition of claim 1, wherein the oily phase comprises from 8 to 60% by weight with respect to the total weight of the composition.

8. The composition of claim 1, wherein the amount of polyol alkyl ester(s) comprises from 0.05 to 5% by weight with respect to the total weight of the composition.

9. The composition of claim 1, further comprising at least one filler.

10. The composition of claim 9, wherein the amount of filler(s) comprises from 0.01% to 15% by weight with respect to the total weight of the composition.

11. The composition of claim 1, having a viscosity, measured at approximately 25° C. using a Rheomat Metler viscometer equipped with a 2 or 3 rotor, ranging from 0.2 to 3 Pa·s.

12. A method of caring for, making up, removing make-up from and/or cleansing the skin, mucous membranes and/or hair, comprising applying the composition of claim 1 to skin, mucous membranes and/or hair.

13. The method of claim 11, wherein the composition is applied to dry skin.

14. A method of preparing the composition of claim 1, comprising combining the aqueous phase, oily phase and silicone emulsifier.

* * * * *